United States Patent
Bastia

(10) Patent No.: US 10,238,328 B2
(45) Date of Patent: Mar. 26, 2019

(54) SYSTEM AND A PROCESSING METHOD

(71) Applicant: THD S.P.A., Correggio (Reggio Emilia) (IT)

(72) Inventor: Filippo Bastia, Soliera (IT)

(73) Assignee: THD S.P.A., Correggio (IT)

(*) Notice: Subject to any disclaimer, the term of this patent is extended or adjusted under 35 U.S.C. 154(b) by 317 days.

(21) Appl. No.: 15/159,262

(22) Filed: May 19, 2016

(65) Prior Publication Data

US 2016/0338633 A1    Nov. 24, 2016

(30) Foreign Application Priority Data

May 20, 2015 (IT) .................. 102015000016098

(51) Int. Cl.
| | |
|---|---|
| *A61B 5/22* | (2006.01) |
| *A61B 5/11* | (2006.01) |
| *A61B 5/00* | (2006.01) |
| *A61B 5/03* | (2006.01) |

(52) U.S. Cl.
CPC .............. *A61B 5/227* (2013.01); *A61B 5/036* (2013.01); *A61B 5/1107* (2013.01); *A61B 5/4255* (2013.01); *A61B 5/6847* (2013.01); *A61B 5/7203* (2013.01); *A61B 5/7278* (2013.01); *A61B 5/7475* (2013.01); *A61B 5/7495* (2013.01); *A61B 2562/0247* (2013.01); *A61B 2562/0261* (2013.01); *A61B 2562/168* (2013.01)

(58) Field of Classification Search
CPC ..... A61B 5/227; A61B 5/1107; A61B 5/4255; A61B 2562/0247
See application file for complete search history.

(56) References Cited

U.S. PATENT DOCUMENTS

| | | | |
|---|---|---|---|
| 2009/0024001 A1* | 1/2009 | Parks | A61B 5/227 606/191 |
| 2012/0130281 A1 | 5/2012 | Ahn | |
| 2013/0158365 A1 | 6/2013 | Chey et al. | |
| 2014/0058288 A1 | 2/2014 | Bartol et al. | |
| 2017/0119267 A1* | 5/2017 | Joo | A61B 5/037 |

FOREIGN PATENT DOCUMENTS

WO    2011011085 A1    1/2011

* cited by examiner

*Primary Examiner* — David J. McCrosky
(74) *Attorney, Agent, or Firm* — Pearne & Gordon LLP

(57) ABSTRACT

A system for processing the manometric measurements carried out by way of an anorectal probe includes one or more processing units, which include: an acquisition module configured for acquiring management parameters of an anorectal manometry; a basal module configured for processing the manometric measurements acquired during the basal maneuver of anorectal manometry in accordance with the management parameters; a squeeze module configured for processing the manometric measurements acquired during the squeeze maneuver; an endurance module, configured for calculating the time interval between the instant at which a maximum value is measured during the squeeze maneuver, and the instant at which the pressure measured falls below a squeeze threshold; a strain module configured for processing the manometric measurements acquired during the strain maneuver; and a memory module configured for the registration of functions and/or indexes calculated by the modules while processing said measures.

10 Claims, 3 Drawing Sheets

SYSTEM AND A PROCESSING METHOD

FIELD OF THE INVENTION

The invention relates to a system and a method for processing measurements performed via anorectal probes.

The invention is devised to be used in clinical examinations effected through anorectal manometry.

DESCRIPTION OF RELATED ART

At present, different types of examinations are performed for clinically evaluating the state of health of the anal sphincter, which include the manometric measurement being aimed at evaluating capability of the sphincter muscles to exert sufficient clamping pressure to hold solids, liquids and gases.

The manometric measurement is carried out via probes that are introduced into the anal canal.

Measuring stations for anorectal manometry are known which are provided with a trolley, which measuring stations, when a clinical examination is to be effected, are brought near the bed whereon the patient is lying.

These stations include a complex equipment formed by one or more probes, as well as by apparatuses intended for probes operation and reading of the pressures acting within the sphincter, the equipment being further formed by an electronic processor for display and recording.

The known solution, in addition to being expensive, is awkward and less versatile. For the purposes of examination, the station must be located in close proximity of the patient's bed indeed, thus constituting an encumbrance that limits the physician's operating space.

In addition, during the examination, in order that measuring stations for anorectal manometry can be activated, the physician needs to move repeatedly within the space between the patient and said station which again is rather inconvenient.

Furthermore, the known solution does not allow the data acquired to be processed and managed on the basis of the physician's needs.

In this context, the technical task underlying the present invention is to propose a system and a processing method which is able to overcome the drawbacks of the prior art.

SUMMARY OF THE INVENTION

The technical task mentioned is attained by a processing system and a processing method realized according to the subject matter of the appended claims.

BRIEF DESCRIPTION OF THE DRAWINGS

Further characteristics and advantages of the present invention will become more apparent from the indicative and therefore non-limiting description of a preferred but non-exclusive embodiment of the processing system illustrated in the appended drawings wherein.

DETAILED DESCRIPTION OF PREFERRED EMBODIMENTS OF THE INVENTION

Figure 1:
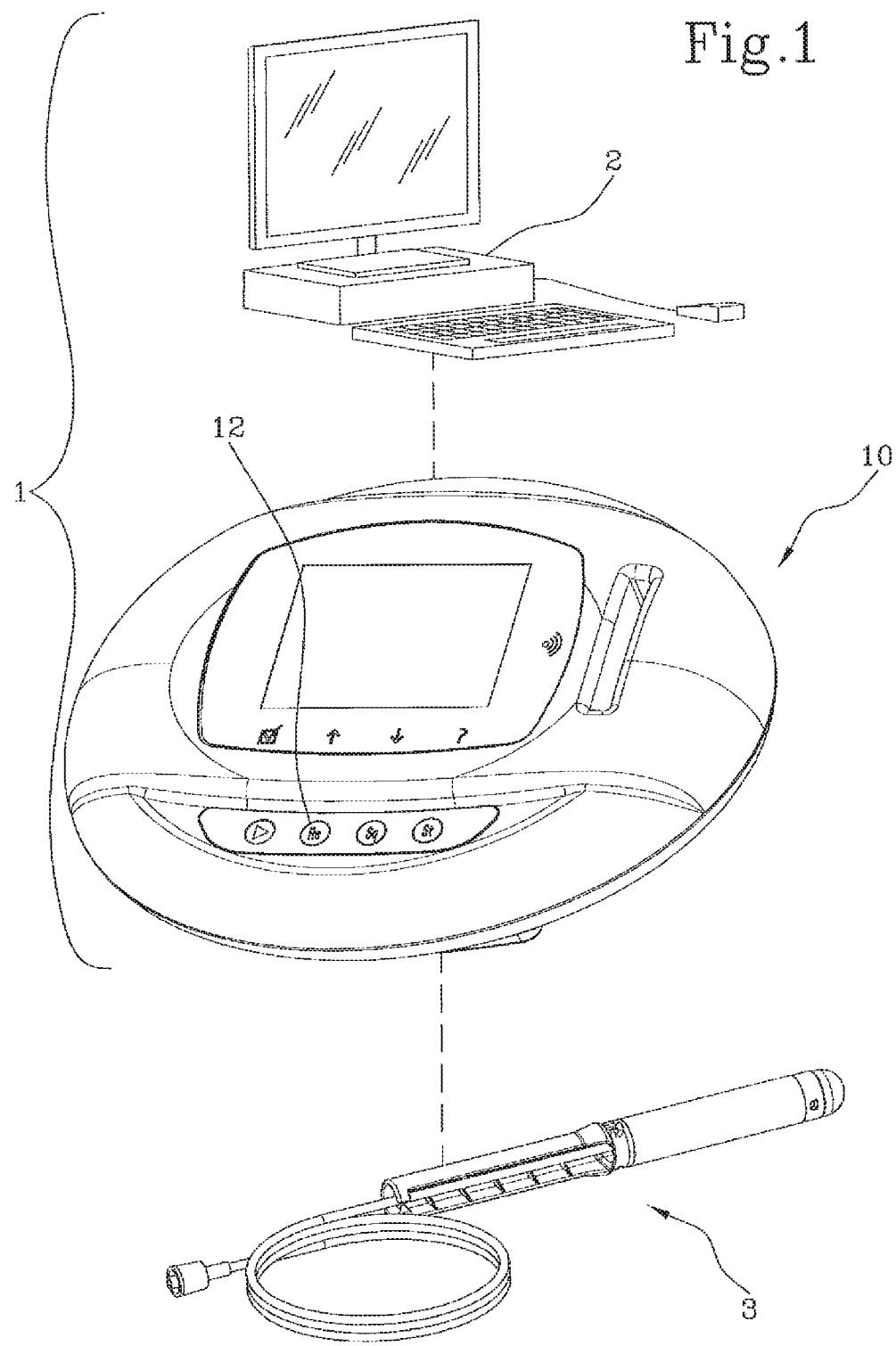
FIG. 1 shows the main components of the processing system of the invention.

With reference to the accompanying figures, by the numeral 1 it is indicated the processing system of the invention.

The system 1 herein provided was devised to perform manometric measurements using an anorectal probe 3.

Preferably, the anorectal probe 3 is of the pneumatic type and includes a main body and an extensible membrane, which is tightly associated with said main body.

The system 1 of the invention includes one or more processing units provided with operating modules intended for processing pressure measurements acquired by the probe 3.

Generally, it should be appreciated that in the present description the processing unit is exhibited as divided into distinct functional modules for the purpose of describing operation thereof in a clear and complete manner.

In practice, such a processing unit may be constituted by a single device or apparatus or suitably programmed electronic system to perform the described features.

The various modules may correspond to hardware entities and/or software routines. Alternatively or in addition, such features may be carried out by a plurality of electronic devices, whereon aforesaid functional modules can be distributed. In detail, the processing unit may use one or more microprocessors or microcontrollers or the like for the execution of instructions contained, for example, within memory modules.

In the preferred embodiment, shown in the accompanying figures, the system 1 comprises an electronic measuring apparatus 10 connectable to an anorectal probe 3. In this case, the apparatus 10 of the invention is of the portable type and is capable of connecting to the processing means 2 such as a personal computer (PC) 2, a tablet or the like.

In particular, the portable apparatus 10 may be connected to the PC 2 via W-Fi or BLUETOOTH wireless technology, etc.

In detail, the apparatus 10 may be a portable tester which may include its own processing unit, the means necessary for the operation and piloting of the probe 3, the sensor means adapted to acquire the diagnostic data, a protective casing, any feed means, interface means, and so on.

In the preferred embodiment of the invention, wherein there is provided use of the portable apparatus 10, the proposed system 1 may comprise a first processing unit included in the apparatus 10 and at least a second processing unit distinct from the first one and included in the PC 2 or in a similar electronic means to which the apparatus 10 is connected. Advantageously, the invention includes at least the six operating modules 11, 21, 22, 23, 24, 25 described below (see FIG. 2), included or embedded in one or more processing units.

First of all, the proposed system 1 comprises an acquisition module 11 configured to acquire anorectal manometry management parameters.

In detail, the acquired parameters are set by the operator, usually a physician.

Figure 2:
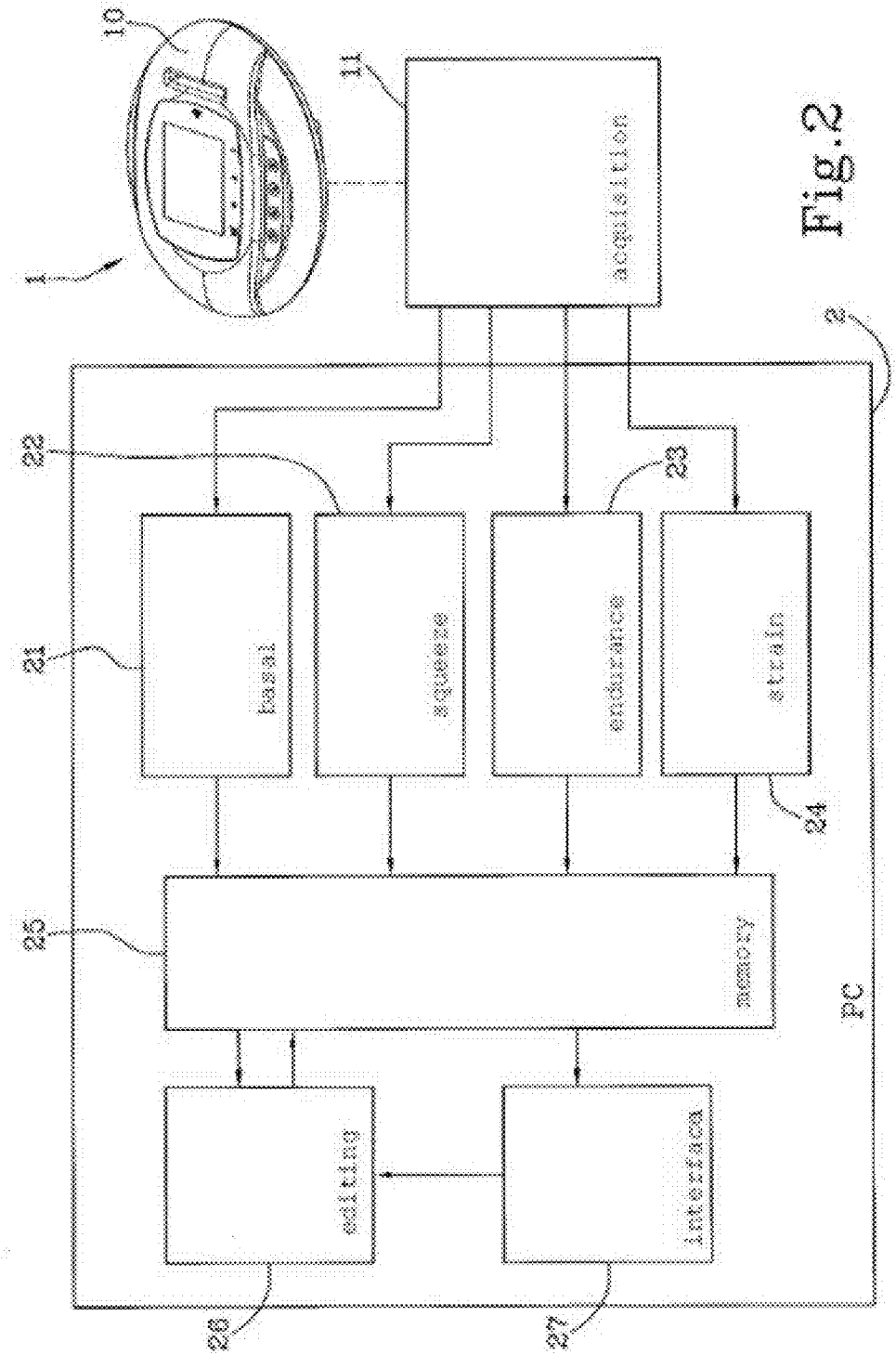
FIG. 2 is a schematic representation of the operating and memory modules used in the invention.

In the case where the invention provides for the above-mentioned portable apparatus 10, the above-mentioned acquisition module 11 is preferably included within the apparatus 10 itself (see FIG. 2).

Additional operating modules may be included in a PC 2 (or similar processing devices), to which the apparatus 10 is connected; however different combinations are also possible.

In detail, the apparatus 10 may be provided with interface means, e.g. comprising keypads or a touch screen display or a reader for RFID transponders, etc., via which said management parameters are set by the operator.

Some possible management parameters acquired from the system 1 may consist of the following: the selection of "maneuvers" that the patient has to perform during examination, the moment at which the processing performed by the pressure measurements units acquired by the probe 3 initiates, particularly in relation to the execution of a certain type of maneuver, and the moment at which such processing terminates.

In the example shown, the portable device 10 is provided with buttons 12, via which the user can select the type of operation and at same time to start or stop the processing; this aspect will be described in detail in a later section.

A second operating module is the basal module 21 that is configured for processing the manometric measurements acquired during the basal maneuver of anorectal manometry, in accordance with said management parameters. As known, the basal tone of the anorectal canal is the one that is exhibited by the anorectal canal in its rest conditions, i.e. when the patient is relaxed.

The invention further provides a squeeze module 22 configured for processing the manometric measurements acquired during the squeeze maneuver in accordance with the above parameters.

During the squeeze maneuver, the patient simulates voluntary withholding of stool by contracting the anorectal muscles.

The proposed system 1 further comprises an endurance module 23, configured for calculating the time interval between the instant at which a maximum value is measured during the squeeze maneuver and the instant at which the measured pressure falls below a squeeze threshold.

The squeeze threshold can be equal to or lower than 90 percent of said maximum value.

In detail, the squeeze threshold can be comprised between 10 and 80 percent of said maximum value, preferably between 40 and 60 percent of said maximum value, and more preferably equal to 50 percent.

It is further provided a strain module 24 configured for processing the manometric measurements acquired during the strain maneuver in accordance with the above parameters.

As known, the strain or Valsalva maneuver consists in simulating the voluntary extrusion of the stool by the examined patient.

The system 1 further comprises a memory module 25 configured for the registration of functions and/or indexes calculated by the operating modules described above following processing of the pressure measurements acquired at different stages of the examination, which correspond to the maneuvers illustrated above.

In practice, thanks to the use of respective dedicated modules, the processing unit is especially configured for calculating the pressure behavior measured by the probe 3 as a function of time, in particular in the course of the various maneuvers.

Figure 3:
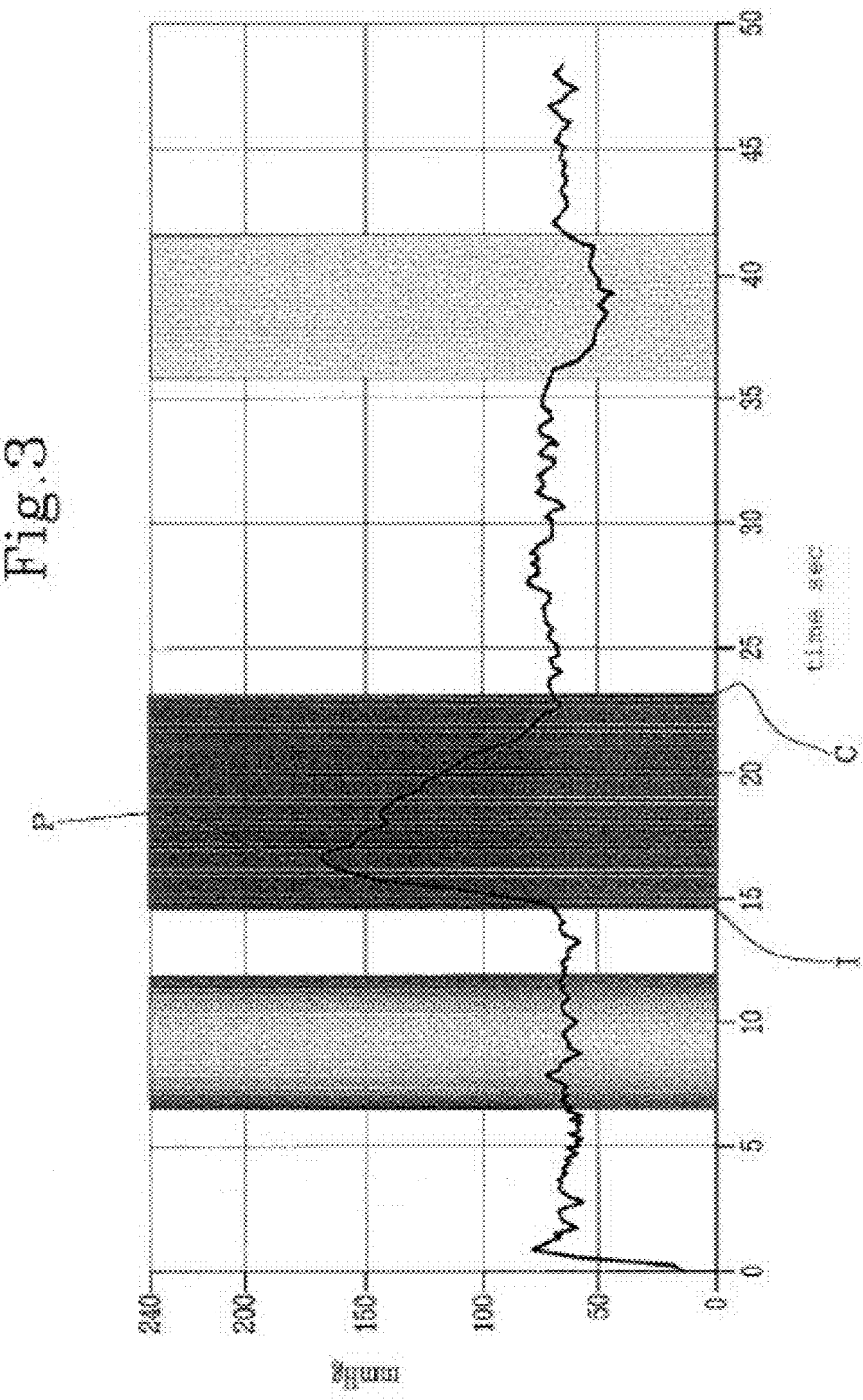
FIG. 3 is a graph showing the temporal course of the pressure measured by way of an anorectal probe and processed by the system of the invention.

The function F that describes the pressure behavior over time may be displayed to the operator via an interface that can show such processing in the form of a chart to be displayed via display or screens or the like (see FIG. 3).

In addition, the above-described operational modules are configured for calculating characteristic indices of the examination effected, such as mean values, maximum values, minimum values and/or time intervals between different values, within their respective maneuvers performed during manometry examination.

To be precise, the indices are in general a function of above mentioned management parameters, which are set by the operator, for example the moment at which detection of the specific measure begins and terminates.

In practice, based on pressure behavior over time (see function F of FIG. 3), and based on the instants at which a maneuver (or the entire examination) starts or ends, which instants are respectively defined as S and E, the processing unit may calculate the characteristic indices such as the maximum pressure value P (or "peak") during the squeeze maneuver.

In a preferred embodiment of the invention, the processing unit comprises calculating means configured to determine a sphincters tonicity index equal to the ratio between a squeeze maximum pressure value and a squeeze resting (or "basal") pressure value.

In detail, this tonicity index is calculated according to a pre-determined measurement time period (e.g. 15 seconds), between the moment the patient carry out a voluntary retention contraction and when he relaxes his muscles, particularly the external sphincter.

Since the squeeze maneuver is especially conditioned by the tonicity of the external sphincter, while the resting muscle tone is especially conditioned by the integrity and tonicity of the internal sphincter, said tonicity index renders the level of tonicity of the external sphincter with respect to the basal tone, i.e. when the patient is resting.

Preferably, the processing unit comprises calculating means configured to determine an external sphincter health index, equal to the ratio between a squeeze maximum pressure value and a squeeze mean pressure value.

Squeeze mean pressure value is the mean (or average) squeeze pressure calculated in a measurement interval.

Basically, the squeeze mean pressure value is calculated as the ratio between the integral of the function of the pressure over time and the extension of said measurement interval.

The more said ratio is close to 1 the more the external sphincter is healthy.

Further, the processing unit can comprise calculating means for determine an health index of the group sphincters/pelvic floor, by means of measures carried out during the strain maneuvers, during a preset measurement interval.

This health index is equal to the ratio between a strain mean pressure and a resting pressure minus 1.

Strain mean pressure is equal to the pressure mean value in the preset measurement interval.

Basically, the strain mean value is calculated as the ratio between the integral of the function of the pressure over time and the value of said measurement interval.

According to whether this index is positive or negative and to the value of the offset between 1 and said ratio, one can evaluate a possible dyssynergic activity between sphincters and pelvic floor.

However, in order to allow the maximum flexibility in use and in order to correct any errors, the invention advantageously provides an editing (or "post-processing") module 26, which is configured for allowing the operator to modify said characteristic indices or, at least, the functions describing the pressure behavior over time.

In detail, the operator may act on the processing unit, and in particular on the editing module 26, via a dedicated user interface 27.

In practice, after completion of the clinical examination, the operator has available the profile of the measured pressure, for example in the form of a graph as shown in FIG. 3, based on which the operator is able to identify the time of beginning and the time of end of individual maneuvers and the examination in its entirety.

By means of the user interface 27, which is acting on the editing module 26, the user may re-set this time of beginning and time of end in order that any artifacts or errors are prevented, which sometimes occur during this type of examination.

Following this resetting, the processing unit recalculates the characteristic indices defined above as a function of the reset time of beginning and time of end and more generally as a function of the modified management parameters. In practice, where the time of beginning of the squeeze maneuver is changed for the purpose of excluding a peak resulting as non-relevant, then a new squeeze average value will be automatically recalculated, which does not take into account the excluded values; if the peak is the one corresponding to the maximum pressure value, i.e. the highest peak, then the processing unit further recalculates the endurance value as defined above.

The system 1 may include a file or database on the basis of which, to each patient there are associated all processing related to all the examinations effected so that the operator is able to verify how the clinical situation of the patient is evolving, as well as perform comparisons, statistical activities, and so on.

Here below operation of the invention is disclosed.

When the physician is ready to perform an anal manometry, the physician takes the device 10 and connects it to a computer such as a desktop PC, and then connects an anorectal probe 3 to the apparatus 10.

Through the user interface 27 provided in said PC and owing to aforementioned archive, the physician provides to record the data of the patient to whom the measures resulting from the examination correspond or alternatively, if patient's data are already recorded in the archive, the physician retrieves the record associated to that patient.

In this way, during the examination, all the measurements and calculations performed will be automatically associated with the patient and stored in the archive, wherein said measurements and calculations are connected to the record of that patient.

At this point, the physician provided with the apparatus 10, comes near to the bed whereon the patient is lying and inserts the probe 3 into the patient's rectum for the purposes of acquiring the measurements required. Each time the patient performs a maneuver provided by the examination, the physician pushes a dedicated button 12 in order to set the instant of start of that maneuver; at the conclusion of the maneuver, the physician again pushes the button 12, thus setting the instant at which the maneuver has terminated.

This operation is repeated cyclically for each maneuver.

It should be appreciated that, because the system 1 provides the portable apparatus 10 described above, the system 1 fully overcomes all the drawbacks due to overall dimensions and inconvenience of the prior art.

Once the examination is completed, the physician puts away the apparatus 10 and the probe 3 and operates via the PC 2 only.

In detail, the physician may retrace the examination effected and evaluate the behavior of pressure in the course of the several maneuvers performed, wherein the physician evaluates the characteristic indices calculated by the system 1 as average values, peak values or other indices yet.

The physician may in addition perform post-processing operations by deleting artifacts or errors, thereby allowing recalculation of the characteristic indices.

In this way, the physician can obtain more reliable results than those obtained by the prior art, which are more easily comparable and already predisposed for running statistics for epidemiological purposes or for other purposes. The invention is further configured in a processing method of manometric measurements performed via an anorectal probe 3.

The proposed method comprises the following steps:

acquiring manometric measurements during basal maneuver of anorectal manometry;

processing the measurements relating to the basal maneuver in accordance with the above management parameters established by the operator;

acquiring manometric measurements during the squeeze maneuver;

processing the measurements relating to the squeeze maneuver in accordance with the management parameters;

calculating the time interval between the instant at which a maximum value is measured during the squeeze maneuver, and the instant at which the measured pressure falls below ninety percent of this maximum value;

acquiring manometric measurements during the strain maneuver;

processing the measurements relating to the strain maneuver in accordance with the management parameters; and storing functions and/or characteristic indices of the maneuvers listed above, obtained by processing the respective measurements.

Preferably, the method comprises one or more of the following calculation steps:

calculating a sphincters tonicity index equal to the ratio between a squeeze maximum pressure value and a resting pressure value;

calculating an external sphincter health index, equal to the ratio between a squeeze maximum value and a squeeze mean value, the latter being defined as the pressure mean value in a measurement value;

calculating sphincters and pelvic floor health index, equal to the difference between the ratio between a mean maximum pressure and a resting pressure and one.

The invention preferably provides a post-processing step, wherein the functions and/or characteristic indices mentioned above are modified in order that any artifacts or errors may be corrected and/or the operating parameters are reset retrospectively.

It should be appreciated that respective actions, which represent optional steps of the method of the invention, may correspond to the features of the measurement system 1, in particular as defined by the operating and memory modules mentioned above, which features comprise the apparatus 10 previously disclosed.

The proposed method can be implemented via a computer program executable on a processing system 1, which program can be made available on a medium readable by a computer.

The invention claimed is:

1. A system for processing manometric measurements carried out by an anorectal probe, comprising one or more processing units, characterized in that said processing unit comprises:

at least one acquisition module configured for acquiring management parameters of an anorectal manometry;

a basal module configured for processing the manometric measurements acquired during the basal maneuver of the anorectal manometry, according to said management parameters;

a squeeze module configured for processing the manometric measurements acquired during the squeeze maneuver according to said management parameters;

an endurance module, configured for calculating the time interval between the instant when a maximum value is measured during the squeeze maneuver, and the instant when the pressure measured falls below a squeeze threshold equal to or less than ninety percent of said maximum value;

a strain module configured for processing the manometric measurements acquired during the strain maneuver according to said management parameters; and at least one memory module configured for recording functions and/or indexes calculated by said modules upon processing said measurements.

2. A system according to claim 1, wherein said anorectal probe is of the pneumatic type and includes both a main body and an extensible membrane tightly associated with said main body.

3. A system according to claim 1, further comprising an electronic measuring apparatus, connectable with an anorectal probe, wherein said apparatus is portable and connectable to the processing unit, the apparatus comprising at least said acquisition module.

4. A system according to claim 1, wherein each of said modules is suitable for calculating one or more characteristic indexes based on the measurements performed by said system, which characteristic indexes correspond to one or more of the following quantities: maximum values, minimum values, average values, time intervals.

5. A system according to claim 1, wherein the processing unit comprises at least one of the following calculating means: calculating means for determine a sphincters tonicity index equal to the ratio between a squeeze maximum pressure value and a resting pressure value; calculating means for determine an external sphincter health index, equal to the ratio between a squeeze maximum value and a squeeze mean value, the latter being defined as a mean value in a measurement interval; calculating means for determine a sphincters and pelvic floor health index, equal to the ratio between a strain mean pressure value and a relative resting pressure minus one.

6. A system according to claim 1, further comprising at least one user interface and at least one editing module configured for enabling a user to modify the functions and/or indexes recorded on said memory module via the user interface.

7. A method for processing manometric measurements carried out by means of an anorectal probe, comprising the following steps:
acquiring manometric measurements during a basal maneuver of an anorectal manometry;
processing said measurements of the basal maneuver according to management parameters;
acquiring manometric measurements during a squeeze maneuver of the anorectal manometry;
processing said measurements of the squeeze maneuver according to management parameters;
calculating a time interval between an instant at which a maximum value is measured during the squeeze maneuver, and an instant when the pressure measured falls below ninety percent of said maximum value;
acquiring manometric measurements during a strain maneuver of the anorectal manometry;
processing said measurements of the strain maneuver according to management parameters;
storing functions and/or characteristic indexes relating to said maneuvers, obtained by processing the respective measurements.

8. A method according to claim 7, further comprising one or more of the following calculation steps:
calculating a sphincters tonicity index equal to a ratio between a squeeze maximum pressure value and a resting pressure value;
calculating an external sphincter health index, equal to a ratio between a squeeze maximum value and a squeeze mean value, the latter being defined as a pressure mean value in a measurement value;
calculating a sphincters and pelvic floor health index, equal to a difference between the ratio between a mean maximum pressure and a resting pressure and one.

9. A method according to claim 8, wherein said functions and/or indexes are modified in order to correct artefact or errors and/or reset said management parameters.

10. A non-transitory computer-readable medium storing a program that, when executed, causes a computer to:
acquire manometric measurements during a basal maneuver of an anorectal manometry;
process said measurements of the basal maneuver according to management parameters;
acquire manometric measurements during a squeeze maneuver of the anorectal manometry;
process said measurements of the squeeze maneuver according to management parameters;
calculate a time interval between an instant at which a maximum value is measured during the squeeze maneuver, and an instant when the pressure measured falls below ninety percent of said maximum value;
acquire manometric measurements during a strain maneuver of the anorectal manometry;
process said measurements of the strain maneuver according to management parameters;
store functions and/or characteristic indexes relating to said maneuvers, obtained by processing the respective measurements; and
calculate at least one of the following:
a sphincters tonicity index equal to a ratio between a squeeze maximum pressure value and a resting pressure value;
an external sphincter health index, equal to a ratio between a squeeze maximum value and a squeeze mean value, the latter being defined as a pressure mean value in a measurement value; and
a sphincters and pelvic floor health index, equal to a difference between the ratio between a mean maximum pressure and a resting pressure and one.

* * * * *